(12) United States Patent
Kennedy et al.

(10) Patent No.: US 7,520,947 B2
(45) Date of Patent: Apr. 21, 2009

(54) COBALT ALLOYS, METHODS OF MAKING COBALT ALLOYS, AND IMPLANTS AND ARTICLES OF MANUFACTURE MADE THEREFROM

(75) Inventors: Richard L. Kennedy, Monroe, NC (US); Henry E. Lippard, Monroe, NC (US)

(73) Assignee: ATI Properties, Inc., Albany, OR (US)

( * ) Notice: Subject to any disclaimer, the term of this patent is extended or adjusted under 35 U.S.C. 154(b) by 800 days.

(21) Appl. No.: 10/444,791

(22) Filed: May 23, 2003

(65) Prior Publication Data

US 2004/0236433 A1 Nov. 25, 2004

(51) Int. Cl.
C22F 1/10 (2006.01)
C22C 19/07 (2006.01)
A61F 2/28 (2006.01)
(52) U.S. Cl. .................. 148/674; 420/436; 623/23.53
(58) Field of Classification Search ................ None
See application file for complete search history.

(56) References Cited

U.S. PATENT DOCUMENTS

| | | | |
|---|---|---|---|
| 2,486,576 A | 11/1949 | Savage | |
| 2,524,661 A | 10/1950 | Harder et al. | |
| 2,678,894 A * | 5/1954 | Harder et al. | 148/707 |
| 3,317,285 A * | 5/1967 | Alexander et al. | 75/235 |
| 3,356,542 A | 12/1967 | Smith | |
| 3,723,995 A | 4/1973 | Baumann | |
| 3,767,385 A * | 10/1973 | Slaney | 420/585 |
| 3,839,024 A | 10/1974 | Demo, Jr. et al. | |
| 3,865,585 A | 2/1975 | Rademacher | |
| 3,970,445 A | 7/1976 | Gale et al. | |
| 3,983,916 A | 10/1976 | Henmi et al. | |
| 3,989,557 A | 11/1976 | Henmi et al. | |
| 4,116,724 A * | 9/1978 | Hirschfeld et al. | 148/674 |
| 4,152,181 A | 5/1979 | Hirakis | |
| 4,581,913 A | 4/1986 | Reed | |
| 4,591,393 A | 5/1986 | Kane et al. | |
| 4,614,550 A | 9/1986 | Leonard et al. | |
| 4,687,487 A | 8/1987 | Hintermann | |
| 4,714,468 A | 12/1987 | Wang et al. | |
| 4,714,469 A * | 12/1987 | Kenna | 606/61 |
| 4,775,426 A | 10/1988 | Murley et al. | |
| 4,789,412 A | 12/1988 | Nakamura et al. | |
| 4,908,033 A | 3/1990 | Frey et al. | |
| 4,908,069 A | 3/1990 | Doherty et al. | |
| 4,919,660 A | 4/1990 | Peilloud | |
| 5,169,463 A | 12/1992 | Doherty et al. | |
| 5,180,394 A | 1/1993 | Davidson | |
| 5,308,412 A | 5/1994 | Shetty et al. | |
| 5,360,496 A | 11/1994 | Kuhlman et al. | |
| 5,399,207 A | 3/1995 | Kemp | |
| 5,462,575 A | 10/1995 | Del Corso | |
| 5,515,590 A | 5/1996 | Pienkowski | |
| 5,592,840 A | 1/1997 | Miyasaka | |
| RE35,863 E | 7/1998 | Sachdeva et al. | |
| 5,782,923 A | 7/1998 | Engelbrecht et al. | |
| 5,816,088 A | 10/1998 | Yamada et al. | |
| 5,824,077 A | 10/1998 | Mayer | |
| 5,891,191 A * | 4/1999 | Stinson | 623/1.2 |
| 5,904,720 A | 5/1999 | Farrar et al. | |
| 5,989,294 A | 11/1999 | Marlow | |
| 6,025,536 A | 2/2000 | Bender et al. | |
| 6,038,900 A | 3/2000 | Miyasaka | |
| 6,045,909 A | 4/2000 | Wang et al. | |
| 6,059,830 A | 5/2000 | Lippincott et al. | |
| 6,067,701 A | 5/2000 | Vandewalle | |
| 6,187,045 B1 | 2/2001 | Fehring et al. | |
| 6,261,322 B1 | 7/2001 | Despres, III et al. | |
| 6,290,726 B1 | 9/2001 | Pope et al. | |
| 6,390,924 B1 | 5/2002 | Yoshida et al. | |

(Continued)

FOREIGN PATENT DOCUMENTS

EP 0 804 934 A2 11/1997

(Continued)

OTHER PUBLICATIONS

Davis et al., The ASM Handbook, Cobalt and Cobalt Alloys, Oct. 31, 1990, vol. 2, pp. 446-454.*

(Continued)

*Primary Examiner*—John P. Sheehan
*Assistant Examiner*—Jessee R. Roe
(74) *Attorney, Agent, or Firm*—Kirkpatrick & Lockhart, Preston, Gates Ellis, LLP; Patrick J. Viccaro; John E. Grosselin, III (57) ABSTRACT

Embodiments of the present invention provide methods of processing cobalt alloys including, in weight percent, from 26 to 30 chromium, from 5 to 7 molybdenum, and greater than 50 cobalt, the methods comprises cold working and aging the alloys such that after aging the cobalt alloys have a hardness of at least Rockwell C 50. Other embodiments provide methods of selectively cold working at least one portion of a cobalt alloy, and subsequently aging the alloy, such after aging, the selectively cold worked portions of the alloy have a higher hardness value then portions of the alloy that were not selectively cold worked. The present invention also discloses cobalt alloys, implants, and articles of manufacture made from cobalt alloys within the present invention.

23 Claims, 1 Drawing Sheet

U.S. PATENT DOCUMENTS

| | | | |
|---|---|---|---|
| 6,395,327 | B1 | 5/2002 | Shetty |
| 6,409,852 | B1 | 6/2002 | Lin et al. |
| 2002/0016635 | A1 | 2/2002 | Despres, III et al. |
| 2002/0127328 | A1 | 9/2002 | Shetty |
| 2002/0151983 | A1 | 10/2002 | Shetty |
| 2003/0000603 | A1 | 1/2003 | Rateick, Jr. et al. |
| 2003/0009215 | A1 | 1/2003 | Mayer |
| 2004/0148033 | A1 | 7/2004 | Schroeder |

FOREIGN PATENT DOCUMENTS

| | | | |
|---|---|---|---|
| GB | 2000188 B | | 8/1982 |
| JP | 62-37355 | * | 2/1987 |
| JP | 2002-363675 | * | 12/2002 |
| JP | 2004-269994 A | | 9/2004 |

OTHER PUBLICATIONS

"ASTM 1537-00: Standard Specification for Wrought Cobalt-28Chromium—6Molybdenum Alloys for Surgical Implants (UNS R31537, UNS R31538, and UNS R31539)," ASTM International, Jan. 9, 2001, pp. 1-3.

A. Varma et al., "Novel Synthesis of Orthopaedic Implant Materials," *Advanced Engineering Materials*, vol. 4, No. 7, (2002) pp. 482-487.

A. Beltran "Chapter 5: Cobalt-Base Alloys," *Superalloys II*, Chester Sims et al. Eds., John Wiley & Sons, New York (1987), pp. 135-163.

"Chapter 5, The Physical and Mechanical Properties of Cobalt," *Cobalt Monograph*, Battelle Memorial Institute, (1960), pp. 73-81.

"ASTM Designation: E8-01: Standard Test Methods for Tension Testing of Metallic Materials" ASTM International, pp. 1-22.

"ASTM Designation E18-02: Standard Test Methods for Rockwell Hardness and Rockwell Superficial Hardness of Metallic Materials" ASTM International, (2003), pp. 1-15.

"ASTM Designation E384-99: Standard Test Method for Microindentation Hardness of Materials", ASTM International, (2003), pp. 1-24.

Rishi Pal Singh and Roger D. Doherty, "Strengthening in Multiphase (MP35N) Alloy: Part I. Ambient Temperature Deformation and Recrystallization," *Metallurgical Transactions A*, vol. 23A, Jan. 1992, pp. 307-319.

N. J. Taylor and R. B. Waterhouse, "A Study of the Ageing Behaviour of a Cobalt Based Implant Alloy," *Journal of Materials Science*, 18 (1983), pp. 3265-3280.

J. B. Vander Sande, J. R. Coke, and J. Wulff, "A Transmission Electron Microscopy Study of the Mechanisms of Strengthening in Heat-Treated Co-Cr-Mo-C Alloys," *Metallurgical Transactions*, vol. 7A, Mar. 1976, pp. 389-397.

P. Huang and H. F. López, "Effects of Grain Size on Development of Athermal and Strain Induced Martensite in Co-Cr-Mo Implant Alloy," *Materials Science and Technology*, Feb. 1999, vol. 15, pp. 157-164.

J. W. Weeton and R. A. Signorelli, "Effect of Heat Treatment Upon Micro-Structures, Microconstituents, and hardness of a Wrought Cobalt Base Alloy," *Transactions of the ASM*, vol. 47, pp. 815-852.

A. Salinas-Rodriguez and J. L. Rodriguez-Galicia, "Deformation Behavior of Low-Carbon Co-Cr-Mo Alloys for Low-Friction Implant Applications," *Journal of Biomedical Materials Research*, vol. 31, (1996), 409-419.

William D. Callister, Jr., *Materials Science and Engineering: An Introduction*, John Wiley & Sons, Inc. (1991), pp. 32-36.

Lippard, H. E. and Kennedy, R. L, "Process Metallurgy of Wrought CoCrMo Alloy," *ASTM Special Technical Publication, STP 1365 Cobalt-Base Alloys for Biomedical Applications*, (1999) pp. 98-107.

Zhuang, L. Z. and Langer, E. W., "Determination of Cyclic Strain-Hardening Behaviour Produced During Fatigue Crack Growth in Cast Co-Cr-Mo Alloy Used for Surgical Implants," *Materials Science and Engineering*, A108 (1989) pp. 247-252.

Levine, David J., "Metallurgical Relationships of Porous-Coated ASTM F75 Alloys," *ASTM Special Technical Publication 953: Quantitative Characterization and Performance of Porous Implants for Hard Tissue Applications*, Jack E. Lemons, Ed., ASTM (Philidelphia, PA) (1985) pp. 60-73.

Saldivar, A. J. and López, H. F., "Role of Aging on the Martensitic Transofmratino in Cast Colbalt Alloy," *Scripta Materialia*, 45 (2001) pp. 427-433.

Form PCT/IPEA/416, "Notification of Transmittal of the International Preliminary Report on Patentability" & PCT/IPEA/409, "PCT International Preliminary Report on Patentability," PCT/US2004/010066, 13 pages, dated Sep. 19, 2005.

* cited by examiner

Fig. 1

COBALT ALLOYS, METHODS OF MAKING COBALT ALLOYS, AND IMPLANTS AND ARTICLES OF MANUFACTURE MADE THEREFROM

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The various embodiments of the present invention generally relate to cobalt alloys, methods of processing cobalt alloys, and articles of manufacture made therefrom. More particularly, certain embodiments of the invention relate to methods of processing cobalt alloys to increase the tensile strength, yield strength, hardness, wear resistance, and fatigue strength of the alloys. Certain cobalt alloys processed according to various embodiments of the present invention are suitable for use in articles of manufacture, such as, for example, articulating medical implants.

2. Description of Related Art

Cobalt alloys are useful in a variety of applications requiring high tensile and fatigue strength, and/or corrosion resistance. For example, although not limiting herein, applications for which the properties of cobalt alloy are particularly well-suited include medical prosthetic or implant applications. More specifically, the fatigue properties of cobalt alloys are desirable for use in implants subjected to cyclical loading, such as hip or knee joint implants; whereas the corrosion resistant properties of cobalt alloys are desirable for biocompatibility. More particularly, cobalt alloys comprising chromium and molybdenum alloy additions, which are commonly referred to as "cobalt-chrome-moly" or "CoCrMo" alloys, have been widely used in both cast and wrought forms to form the articulating component of both knee and hip joint replacements.

However, one shortcoming of implants made from such conventional cobalt alloys is that the implants can degrade during service due to wear. As used herein the term "wear" means deterioration of at least a portion of a surface due to material removal caused by the relative motion between the at least a portion of the surface and at least a portion of another surface or substance. For example, it is known that certain implant surfaces, or "wear surfaces," are subjected to substantial wear during service. As used herein, the term "wear surface" means at least a portion of a surface that is subjected to wear.

The deterioration of implant wear surfaces can ultimately result in the need to replace the implant. One particular problem associated with the deterioration of implant wear surfaces is the generation of wear debris. As used herein, the term "wear debris" refers to material that is removed from the wear surface during wear. For example, in "metal-on-polymer" articulating joints (i.e., joints wherein a metal surface articulates over a polymer surface), polyethylene wear debris is a principal cause of failures requiring replacement of the implant device. Further, concerns have been reported regarding the long term effects on the human body of small, high surface area alloy wear debris generated from wear of "metal-on-metal" articulating joints (i.e., joints wherein a metal surface articulates over another metal surface) and the elevated serum cobalt and chromium levels observed from wear of such joints.

In addition, the design of implant devices can be limited by the properties of the material used to make the device. For example, in ball and socket joint implants, the range of motion between the ball and the socket may be limited if the implants are made from materials having a relatively low tensile and/or fatigue strength due to the large size of the implant required. In contrast, the same implant made using materials having higher tensile and/or fatigue strengths would allow for a larger margin of safety. Alternatively, the use of higher strength materials could allow for the development of smaller implants with a greater range of motion. Additionally, the use of higher strength materials can permit a device design incorporating a smaller ball size, thereby reducing the volumetric wear rate of a polyethylene cup in a metal-on-polymer joint.

While increasing the hardness of implant wear surfaces can reduce the occurrence of wear-related implant failure by resisting the generation of wear debris during service, attempts to increase the hardness of implants have generally focused on nitriding or coating the surface of the implants. For example, U.S. Pat. No. 5,308,412 to Shetty et al. describes a method of hardening the surface of a cobalt-chromium based orthopedic implant device. The implant device is hardened by exposure to molecular nitrogen gas or ionized nitrogen at a temperature ranging from 500° F. to 2400° F. for a time sufficient to permit the diffusion of nitrogen into the surface of the implant. The nitrogen diffusion results in a hardened diffusion layer and hardened outer surface layer. See Shetty et al. at col. 3, lines 21-28. According to Shetty et al., the Knoop hardness of the implant can be increased up to 5000 KHN depending upon the temperature, time, and nitrogen gas pressure used. See Shetty et al., at col. 6, lines 24-26. U.S. Pat. No. 5,180,394 to Davidson discloses orthopedic implants coated with a wear-resistant coating of zirconium oxide, nitride, carbide, or carbonitride. For example, a zirconium containing alloy surface layer can be applied to a conventional implant material and thereafter treated to form a diffusion-bonded layer of zirconium oxide on the surface of the implant. See Davidson at col. 9, lines 53-57.

Cobalt alloys having improved friction and fatigue properties have also been disclosed. For example, U.S. Pat. No. 6,187,045 B1 to Fehring et al. discloses a cobalt alloy having improved fatigue and friction properties with ultra high molecular weight polyethylene (or "UHMWPE"), which is commonly used, for example, to form socket portions of metal-on-polymer implant devices. In particular, the cobalt alloy of Fehring et al. is essentially free of carbides, nitrides, and sigma second phases that reduce the friction and fatigue properties of the alloy.

However, utilization of coatings on implant devices has not been widespread due to concerns about reliability, and there remains a need for improved cobalt alloys for orthopedic implants that can increase the service life of the implant and reduce the number of revision surgeries necessary to replace failed implants. In particular, it would be desirable to develop cost-effective methods of processing cobalt alloys to increase the tensile strength, yield strength, hardness, wear resistance, and fatigue strength of the cobalt alloys that can be used in conjunction with a variety of cobalt alloy compositions.

BRIEF SUMMARY OF THE INVENTION

Embodiments of the present invention related to methods of processing cobalt alloys. For example, one embodiment provides a method of processing a cobalt alloy comprising from 26 to 30 weight percent chromium, from 5 to 7 weight percent molybdenum, and greater than 50 weight percent cobalt, the method comprising cold working the cobalt alloy and aging the cold worked cobalt alloy at a temperature ranging from 900° F. to 1300° F. for a time period ranging from 1 hour to 24 hours, wherein after aging the cold worked cobalt alloy, the cobalt alloy has a hardness of at least Rockwell C 50. Another embodiment provides a method of selectively hardening a cobalt alloy including from 26 to 30 weight percent chromium, from 5 to 7 weight percent molybdenum, and greater than 50 weight percent cobalt, the method comprising cold working at least one selected portion of the cobalt alloy, and aging the cold worked cobalt alloy at a temperature ranging from 900° F. to 1300° F. for a time period ranging from 1 hour to 24 hours, wherein after aging the cold worked cobalt alloy, the at least one selected portion of the cobalt alloy has a Knoop hardness number of at least 560. Still another embodiment provides a method of processing a cobalt alloy including, in percent by weight, from 26 to 30 chromium, from 5 to 7 molybdenum, up to 0.05 carbon, up to 0.75 nickel, up to 0.35 iron, up to 0.50 silicon, up to 0.50 manganese, up to 0.15 nitrogen, and cobalt, the method comprising cold working the cobalt alloy such that at least a portion of the cobalt alloy-has a hardness of at least Rockwell C 45 after cold working.

Other embodiments of the present invention relate to cobalt alloys. For example, one embodiment provides a cobalt alloy comprising, in percent by weight, up to 0.35 carbon, from 26 to 30 chromium, from 5 to 7 molybdenum, up to 1.0 nickel, up to 0.75 iron, up to 1.0 silicon, up to 1.0 manganese, up to 0.25 nitrogen, and cobalt, wherein at least a portion of the cobalt alloy has a hardness of at least Rockwell C 50.

Still other embodiments of the present invention relate to methods of processing implants. For example, one embodiment provides a method of processing an implant comprising a cobalt alloy, the method comprising cold working at least a portion of the implant and aging the implant after cold working the at least a portion of the implant at a temperature ranging from 900° F to 1300° F. for a time period ranging from 1 hour to 24 hours, wherein after aging the implant, the at least a portion of the implant that was cold worked has a hardness of at least Rockwell C 50. Another embodiment provides a method of processing an implant comprising a cobalt alloy, the method comprising cold working at least a portion of the implant and aging the implant after cold working the at least a portion of the implant at a temperature ranging from 900° F. to 1300° F. for a time period ranging from 1 hour to 24 hours, wherein after aging the implant, the at least a portion of the implant that was cold worked has a Knoop hardness number of at least 560.

Other embodiments of the present invention relate to implants and articles of manufacture. For example, one embodiment provides an implant comprising a cobalt alloy, the cobalt alloy including at least a portion having a hardness of at least Rockwell C 50. Another embodiment provides, an implant comprising a cobalt alloy, the cobalt alloy including at least a portion having a Knoop hardness number of at least 560. Another embodiment provides, an implant comprising a cobalt alloy, the cobalt alloy having a percent elongation of at least 10 percent and including a first portion having a Knoop hardness number of at least 560 and a second portion, adjacent the first portion, the second portion having a Knoop hardness number that is less than the Knoop hardness number of the first portion. Still another embodiment provides an article of manufacture comprising a cobalt alloy comprising, in percent by weight, up to 0.35 carbon, from 26 to 30 chromium, from 5 to 7 molybdenum, up to 1.0 nickel, up to 0.75 iron, up to 1.0 silicon, up to 1.0 manganese, up to 0.25 nitrogen, and cobalt, wherein at least a portion of the alloy has a hardness of at least Rockwell C 50.

BRIEF DESCRIPTION OF THE SEVERAL VIEWS OF THE DRAWING(S)

Certain embodiments of the present invention will be better understood if read in conjunction with the following figure in which.

DETAILED DESCRIPTION OF THE INVENTION

Various embodiments of the present invention are useful in providing cobalt alloys having improved tensile strength, hardness, wear resistance, and fatigue strength as compared to conventionally processed cobalt alloys. Further, certain embodiments of the present invention can be useful in modifying the surface hardness of the cobalt alloys while maintaining a tough, ductile core comparable to conventionally processed cobalt alloys.

Wrought cobalt alloys for use in medical implant devices are typically supplied to implant manufacturers in a several conditions as described in "Standard Specification for Wrought Cobalt-28Chromium-6Molybendum Alloys for Surgical Implants," ASTM F1537-00, American Society for Testing and Materials (2001), which is specifically incorporated herein by reference. For example, a typical processing sequence for a warm worked, wrought cobalt alloy suitable for use in a medical implant is as follows. First, the alloy is melted in an air or vacuum induction process, both of which are well known in the art. The alloy is subsequently refined in a vacuum arc refining or an electro-slag refining operation, as known in the art. The alloy ingot is then thermomechanically processed into bars or shape configurations, which are subsequently provided to the implant manufacturer. The implant manufacturer then forms the wrought cobalt alloy, such as by machining and/or forging the alloy, into the desired configuration.

As described in ASTM F1537-00, wrought alloys in the warm worked condition typically have the highest available tensile strength and hardness, with a minimum tensile strength of approximately 170 kilopounds per square inch ("ksi"), a minimum 0.2%-offset yield strength of approximately 120 ksi, and a typical hardness of approximately Rockwell C 35 ("HRC 35"). As used herein, the term "Rockwell C" or "HRC" followed by a number denotes the hardness of a material as measured by the Rockwell hardness test using the "C-scale," as tested according to ASTM E18-02 which is specifically incorporated by reference herein.

However, as previously discussed, conventionally processed cobalt alloys have limitations related to their tensile strength, yield strength, hardness, wear resistance, and fatigue strength. As discussed below in more detail, various embodiments of the present invention can be advantageous in providing cobalt alloys having one or more of the following: improved tensile strength, improved yield strength, improved hardness, improved wear resistance, and improved fatigue strength as compared to conventionally processed cobalt alloys.

The methods of processing cobalt alloys according to various embodiments of the present invention are useful in processing cobalt alloys including, but not limited to, cobalt alloys containing chromium and molybdenum alloying additions. As will be recognized by those skilled in the art, cobalt alloys that include chromium and molybdenum alloying additions, such as those described in ASTM F 1537-00, are suitable for use in medical or surgical implant devices, or prostheses ("implants"). For example, cobalt alloys that are useful in various embodiments of the present invention include, but are not limited to, cobalt alloys comprising from 26 to 30 weight percent chromium, from 5 to 7 weight percent molybdenum, and greater than 50 weight percent cobalt.

More particularly, specific, non-limiting examples of cobalt alloys that are believed to be useful in various embodiments of the present invention include the alloys designated as "Alloy 1" and "Alloy 2," in Table 1 of ASTM F 1537-00. As described in ASTM F1537-00, "Alloy 1" is a "low carbon alloy" that comprises up to 0.14 weight percent carbon, from 26 to 30 weight percent chromium, from 5 to 7 weight percent molybdenum, up to 1.0 weight percent nickel, up to 0.75 weight percent iron, up to 1.0 weight percent silicon, up to 1.0 weight percent manganese, up to 0.25 weight percent nitrogen, and cobalt. Further, according to ASTM F1537-00, "Alloy 2" is a "high carbon alloy" that comprises from 0.15 to 0.35 weight percent carbon, from 26 to 30 weight percent chromium, from 5 to 7 weight percent molybdenum, up to 1.0 weight percent nickel, up to 0.75 weight percent iron, up to 1.0 weight percent silicon, up to 1.0 weight percent manganese, up to 0.25 weight percent nitrogen, and cobalt.

In one specific, non-limiting example, the cobalt alloy is a cobalt alloy comprising, in percent by weight, up to 0.35 carbon, from 26 to 30 chromium, from 5 to 7 molybdenum, up to 1.0 nickel, up to 0.75 iron, up to 1.0 silicon, up to 1.0 manganese, up to 0.25 nitrogen, and cobalt.

In another specific, non-limiting example, the cobalt alloy is a cobalt alloy comprising, in percent by weight, up to 0.05 carbon, from 26 to 30 chromium, from 5 to 7 molybdenum, up to 0.75 nickel, up to 0.35 iron, up to 0.50 silicon, up to 0.50 manganese, up to 0.15 nitrogen, and cobalt.

Other non-limiting examples of cobalt alloys that are believed to be useful according various non-limiting embodiments of the present invention include those compositions disclosed in U.S. Pat. No. 6,187,045 B1, the disclosure of which is specifically incorporated by reference herein.

As previously discussed, one advantage of processing cobalt alloys in accordance with various embodiments of the present invention is that the cobalt alloys can have improved tensile strength, yield strength, hardness, wear resistance, and fatigue strength. In one non-limiting embodiment according to the present invention, there is provided a method of processing a cobalt alloy comprising cold working a cobalt alloy which includes from 26 to 30 weight percent chromium, from 5 to 7 weight percent molybdenum, and greater than 50 weight percent cobalt, such that after cold working, the cobalt alloy has an increased hardness. Non-limiting examples of suitable methods of cold working include, rolling, drawing, swaging, shot peening, and laser peening.

In one specific, non-limiting embodiment of the present invention, cold working the cobalt alloy comprises cold drawing the cobalt alloy. Although not required, cold drawing can be conducted such that the cobalt alloy has a total reduction in area ranging from 5 percent to 40 percent. In some non-limiting embodiments, cold drawing is conducted such that the cobalt alloy has a total reduction in area ranging from 10 percent to 25 percent.

In another specific, non-limiting embodiment, cold working the cobalt alloy comprises cold rolling the cobalt alloy. Although not required, cold rolling can be conducted such that the alloy has a total reduction in thickness ranging from 5 percent to 40 percent. In some non-limiting embodiments, cold rolling is conducted such that the cobalt alloy has a total reduction in thickness ranging from 10 percent to 25 percent.

Cold working a cobalt alloy will result in an increase in dislocation density in the material, which in turn will generally result in an increase in the ultimate tensile strength, yield strength, and hardness of the alloy, while generally decreasing the ductility of the alloy. Further, cold working certain cobalt alloys comprising a matrix phase having a face centered cubic ("fcc") crystal structure (or "fcc phase") can result in an at least partial transformation of the fcc phase to a phase having a hexagonal close packed ("hcp") crystal structure (or "hcp phase"), which can also result in increases in the hardness and strength of the material. The orientation of atoms in these crystal structures are well known in the art, for example, see William Callister, Jr., *Materials Science and Engineering: An Indroduction, 2$^{nd}$ Ed.*, John Wiley & Sons, Inc., New York (1991) at pages 32-36, which are specifically incorporated by reference herein.

It will be appreciated by those skilled in the art that cobalt and many cobalt alloys have an fcc phase that is generally stable at elevated temperatures and which can be stabilized at lower temperatures, such as room temperature, by the addition of certain types and amounts of alloying elements. Further, it is known that cobalt and many cobalt alloys have an hcp phase that is generally stable at lower temperatures than the fcc phase. See Chester Sims et al., *Superalloys II*, John Wiley & Sons, Inc., New York (1987) at pages 140-142, which are specifically incorporated by reference herein. Conventional cobalt alloys having the compositions designated in ASTM F1537-00 as "Alloy 1 " and "Alloy 2" will predominately comprise the fcc phase at room temperature due, in part, to the type and amount of alloying additions and the processing history of the material. Accordingly, implants made from such conventional cobalt alloys will have the wear and hardness properties associated with the fcc phase. Although not intending to be bound by any particular theory, it is believed by the inventors that by appropriately cold working these alloys, the fcc phase can be at least partially transformed to the hcp phase, which can result in an increase in the hardness and strength of the cobalt alloy.

For certain applications, the properties of the cobalt alloy after cold working will be sufficient such that no further processing of the alloy is required. For example, one non-limiting embodiment of the present invention comprises processing a cobalt alloy including, in percent by weight, from 26 to 30 chromium, from 5 to 7 molybdenum, up to 0.05 carbon, up to 0.75 nickel, up to 0.35 iron, up to 0.50 silicon, up to 0.50 manganese, up to 0.15 nitrogen, and cobalt, by cold working the cobalt alloy such that at least a portion of the cobalt alloy has a hardness of at least Rockwell C 45 after cold working. However, as discussed below, for other applications additional processing of the cobalt alloy may be desired to further increase the tensile strength, yield strength, hardness, wear resistance, or fatigue strength of the cobalt alloy, while maintaining at least a minimum level of ductility in the alloy.

Accordingly, after cold working the cobalt alloy as discussed above, in some non-limiting embodiments of the present invention, the cobalt alloy is aged to further increase the desired properties as compared to the cold worked, but unaged cobalt alloy. For example, although not limiting herein, the cold worked cobalt alloy can be aged to further increase one or more of the following properties: tensile strength, yield strength, hardness, wear resistance, and fatigue strength, while maintaining at least a minimum level of ductility in the alloy.

While not intending to be bound by any particular theory, the increases in tensile strength, yield strength, hardness, wear resistance, and/or fatigue strength of the cobalt alloy after cold working and aging are believed to be due to the at least partial transformation of the crystal structure of the cobalt alloy from an fcc phase to an hcp phase during cold working, combined with further structural changes that occur in the alloy upon aging. While the structural changes that occur in the alloy upon aging are not fully understood, it has been observed by the inventors that substantial increases in both the strength and hardness of the alloy after aging the cold worked cobalt alloy can be achieved.

However, both the type and amount of cold work and the aging time and temperature must be controlled to achieve the desired properties. The inventors have observed that if a cold worked cobalt alloy is aged for too long a time at too high of a temperature, the properties of the cold worked cobalt alloy after aging can decrease as compared to the cold worked but unaged cobalt alloy. Again, while not intending to be bound by any particular theory, it is believed that if the cold worked cobalt alloy is aged for too long of a time or at too high of a temperature, the cobalt alloy may undergo recovery and recrystallization during aging, or the hcp phase may develop in an undesirable size and form, which can result in a decrease in the properties discussed above. Further, if sufficient cold work is not introduced into the cobalt alloy, aging may be less effective or, in some cases, ineffective in producing the desired properites.

Accordingly, in one non-limiting embodiment of the present invention, the cold worked cobalt alloy is aged at a temperature ranging from 900° F. to 1300° F. for a time period ranging from 1 hour to 24 hours, such that after aging the cold worked cobalt alloy, the cobalt alloy has a hardness of at least Rockwell C 50. For example, although not limiting herein, after cold working the cobalt alloy according to this embodiment, at least a portion of the cobalt alloy can comprise an hcp crystal structure. Thus, although not limiting herein, the cobalt alloys formed according to this embodiment of the present invention can comprise an fcc phase matrix with one or more regions of hcp phase distributed in the fcc phase matrix.

In another, non-limiting embodiment of the present invention, the cold worked cobalt alloy is aged at a temperature ranging from 1000° F. to 1200° F. for a time period ranging from 1 hour to 24 hours, such that after aging the cold worked cobalt alloy, the cobalt alloy has a hardness of at least Rockwell C 53, a 0.2%-offset yield strength of at least 210 kilopounds per square inch, and a tensile strength of at least 260 kilopounds per square inch.

The present invention further contemplates methods of processing at least one selected portion of the cobalt alloy in order to increase the hardness of the at least one selected portion. For example, one non-limiting embodiment of the present invention provides a method of selectively hardening a cobalt alloy including from 26 to 30 weight percent chromium, from 5 to 7 weight percent molybdenum, and greater than 50 weight percent cobalt. The method comprises cold working at least one selected portion of the cobalt alloy, and subsequently aging the cold worked cobalt alloy at a temperature ranging from 900° F. to 1300° F. for a time period ranging from 1 hour to 24 hours. After aging, the at least one selected portion of the cobalt alloy has a Knoop Hardness Number ("KHN") of at least 560. According to this non-limiting embodiment, the at least one selected portion can include at least a portion of at least one surface of the alloy, and after aging the cold worked cobalt alloy, at least a portion of the at least one surface of the cobalt alloy has a KHN of at least 560.

While not meaning to be bound by any particular theory, it is believed by the inventors that by selectively cold working portions of the cobalt alloy prior to aging, and in particular, cold working surface portions of the alloy, a cobalt alloy having a hardened surface and tough "core" can be produced. As used herein, the term "surface" means the region extending from the exterior of the alloy inwardly approximately 0.4 millimeters ("mm") or less. As used herein, the terms "core" or "subsurface" mean regions interior to the surface of the alloy. For example, at least a portion of at least one surface of the cobalt alloy can be cold worked prior to aging, such that after aging, the at least a portion of the at least one surface of the cobalt alloy has a hardness greater than subsurface or core regions of the cobalt alloy. By selectively cold working the cobalt alloy in this manner prior, the selected portions of the cobalt alloy can have wear properties associated with a hardened alloy, while the cobalt alloy retains much of its bulk ductility. Although not limiting herein, such a structure is believed to be advantageous in imparting both wear resistance and toughness to the cobalt alloy.

For example, one embodiment of the present invention comprises cold working at least one selected portion of a cobalt alloy. Selective cold working can include any method of cold working know in the art that permits processing of selected portions of the cobalt alloy. Examples of suitable methods of cold working at least one selected portion of the cobalt alloy include, but are not limited to: swaging, shot peening, and laser peening. After selectively cold working, the cobalt alloy is aged such that, after aging, the at least one selected portion of the cobalt alloy has a hardness that is higher than an unselected portion of the alloy.

For example, although not limiting herein, at least a portion of at least one surface of a cobalt alloy can be selectively cold worked by shot peening the at least a portion of the at least one surface of the alloy. Thereafter, the cobalt alloy can be aged at a temperature ranging from 900° F. to 1300° F. for a time period ranging from 1 hour to 24 hours. After aging the selectively cold worked cobalt alloy, the at least a portion of the at least one surface of the cobalt alloy that was cold worked can have a KHN of at least 560, whereas an unselected portion of the alloy, which may include subsurface or core regions of the alloy, can have a KHN less than 560. In another non-limiting example, the at least one selected portion of the cobalt alloy can include at least a portion of at least one surface of the alloy that can be selectively cold worked by laser peening.

Knoop hardness measurements are generally conducted in accordance with ASTM E384-99, which is specifically incorporated by reference herein. The Knoop hardness test is generally considered to be a "microindentation" hardness test, which can be used to measure the hardness of specific regions of the alloy that are either too small or too thin to be measured using a "macroindentiation" hardness test, such as the Rockwell hardness test previously described. See ASTM E384-99 at page 3. Accordingly, when the at least one portion of the cobalt alloy selected for cold working includes at least a portion of a surface of the cobalt alloy, Knoop hardness measurements are preferably used to measure the hardness of the at least a portion of the surface of the cobalt alloy after aging.

Alternatively, macroindentation hardness tests, such as the Rockwell hardness tests previously described, can be used to measure the hardness of the at least one selected portion of the alloy when the at least one selected portion includes both surface and subsurface regions and the at least one selected portion has a thickness compatible with the Rockwell hardness test. See ASTM E18-02 at pages 5-6. For example, although not limiting herein, in another embodiment of the present invention, the method for selectively hardening a cobalt alloy including from 26 to 30 weight percent chromium, from 5 to 7 weight percent molybdenum, and greater than 50 weight percent cobalt, comprises cold working at least one selected portion of the cobalt alloy. According to this non-limiting embodiment, the at least one selected portion includes both surface and subsurface regions of the cobalt alloy. After cold working, the cobalt alloy is aged in a furnace at a temperature ranging from 900° F. to 1300° F. for a time period ranging from 1 hour to 24 hours. After aging, the at least one selected portion of the cobalt alloy has a hardness of at least Rockwell C 50.

Various non-limiting embodiments of the present invention further contemplate cobalt alloys as are described below in detail. In one non-limiting embodiment of the present invention, the cobalt alloy comprises, in percent by weight, up to 0.35 carbon, from 26 to 30 chromium, from 5 to 7 molybdenum, up to 1.0 nickel, up to 0.75 iron, up to 1.0 silicon, up to 1.0 manganese, up to 0.25 nitrogen, and cobalt; and has a hardness of at least Rockwell C 50. Although not limiting herein, according to this non-limiting embodiment at least a portion of the alloy can comprise an hcp crystal structure. For example, although not limiting herein, the cobalt alloy can comprise an fcc phase matrix having one or more regions of an hcp phase distributed in the fcc phase matrix. Further, although not limiting herein, the cobalt alloy according to this embodiment of the present invention can be a cold worked and aged alloy. Suitable methods of cold working and aging the alloy are described above in detail.

In another non-limiting embodiment of a cobalt alloy according to the present invention, the cobalt alloy comprises, in percent by weight, up to 0.05 carbon, from 26 to 30 chromium, from 5 to 7 molybdenum, up to 0.75 nickel, up to 0.35 iron, up to 0.50 silicon, up to 0.50 manganese, up to 0.15 nitrogen, and cobalt; wherein at least a portion of the cobalt alloy comprises an hcp crystal structure. For example, although not limiting herein, the cobalt alloy can comprise an fcc phase matrix having one or more regions of an hcp phase distributed in the fcc phase matrix. Further, cobalt alloys according to this non-limiting embodiment can have a hardness of at least Rockwell C 50 and be cold worked and aged.

As previously discussed, cobalt alloys comprising chromium and molybdenum alloying additions are commonly used in medical or surgical implant applications. Non-limiting examples of medical or surgical implants for which these cobalt alloys may be used include: orthopedic implants including, but not limited to, hip and knee joints implants; shoulder implants; spinal components and devices including, but not limited to, articulating components; cardiovascular components and devices including, but not limited to, wires, cables, and stents; and fracture fixation devices including, but not limited to plates and screws. As described below, certain non-limiting embodiments of the present invention contemplate implants comprising cobalt alloys and methods of processing implants comprising cobalt alloys.

One non-limiting embodiment of the present invention provides a method of processing an implant comprising a cobalt alloy. The method according to this non-limiting embodiment comprises cold working at least a portion of the implant, and aging the implant after cold working the at least a portion of the implant at a temperature ranging from 900° F. to 1300° F. for a time period ranging from 1 hour to 24 hours, wherein after aging the implant, the at least a portion of the implant that was cold worked has a hardness of at least Rockwell C 50. Although not limiting herein, the at least a portion of the implant that has a hardness of at least Rockwell C 50 can comprise both surface and subsurface regions of the implant. For example, the at least a portion of the implant that has a hardness of at least Rockwell C 50 can include the at least a portion of a wear surface of the implant and subsurface regions adjacent the wear surface. Alternatively, although not limiting herein, the at least a portion of the implant can include, for example, the "ball" portion of a ball and socket joint implant. Further, the at least a portion of the implant that has a hardness of at least Rockwell C 50 can comprise an fcc phase matrix with one or more regions of an hcp phase distributed in the fcc phase matrix.

In another embodiment, the method of processing an implant comprising a cobalt alloy comprises cold working at least a portion of the implant, and aging the implant after cold working the at least one portion of the implant at a temperature ranging from 900° F. to 1300° F. for a time period ranging from 1 hour to 24 hours, wherein after aging the implant, the at least a portion of the implant that was cold worked has a KHN of at least 560. Although not required, according to this non-limiting embodiment, the at least a portion of the implant that has a KHN of at least 560 can include at least a portion of a wear surface of the implant. Further, the at least a portion of the implant that has a KHN of at least 560 can comprise an fcc phase matrix with one or more regions of an hcp phase distributed in the fcc phase matrix.

Implants according to various, non-limiting embodiments of the present invention will now be discussed. One non-limiting embodiment of the present invention provides an implant comprising a cobalt alloy, wherein the cobalt alloy includes at least a portion having a KHN of at least 560. Although not limiting herein, according to this embodiment, the at least a portion of the cobalt alloy that has a KHN of at least 560 can comprise an fcc phase matrix with one or more regions of an hcp phase distributed in the fcc phase matrix. Further, the cobalt alloy according to this embodiment can be a cold worked and aged alloy.

Furthermore, according to the above embodiment, at least a region of a wear surface of the implant can include the at least a portion of the cobalt alloy having a KHN of at least 560. As previously discussed, the deterioration of implant wear surfaces can be particularly problematic and can result in a failure of the implant. Further, conventional methods of nitriding the surface of cobalt alloys to increase surface hardness can pose reliability concerns with respect to the nitride layer. Therefore, the implants according to this non-limiting embodiment of the present invention can be particularly advantageous in providing wear surfaces having increased hardness, without the need to nitride the surface of the cobalt alloy. Accordingly, although not required, according to this embodiment, the at least a portion of the cobalt alloy having a KHN of at least 560 is an un-nitrided surface comprising less than 5 atomic percent nitrogen.

In another non-limiting embodiment of the present invention, the implant comprises a cobalt alloy, the cobalt alloy including at least a portion having a hardness of at least Rockwell C 50. Although not limiting herein, both surface and subsurface regions of the implant can include the at least a portion of the cobalt alloy having a hardness of at least Rockwell C 50. Further, according to this embodiment, the at least a portion of the cobalt alloy having a hardness of at least Rockwell C 50 can comprise less than 5 atomic percent nitrogen. Although not limiting herein, the cobalt alloy according to this embodiment can be a cold worked and aged alloy.

In still another non-limiting embodiment of an implant according to the present invention, the implant comprises a cobalt alloy including at least a portion having a hardness of at least Rockwell C 50, the at least a portion having a hardness of at least Rockwell C 50 comprising an hcp crystal structure. For example, although not limiting herein, the at least a portion having a hardness of at least Rockwell C 50 can comprise an fcc phase matrix including one or more regions of an hcp phase distributed in the fcc phase matrix.

Cobalt alloys that are suitable for use in the implants according to the present invention include those cobalt alloys previously discussed. For example, although not limiting herein, the cobalt alloy can comprise, in percent by weight, up to 0.35 carbon, from 26 to 30 chromium, from 5 to 7 molybdenum, up to 1.0 nickel, up to 0.75 iron, up to 1.0 silicon, up to 1.0 manganese, up to 0.25 nitrogen, and cobalt.

In another non-limiting embodiment of the present invention, the implant comprises a cobalt alloy comprising, in percent by weight, up to 0.14 carbon, from 26 to 30 chromium, from 5 to 7 molybdenum, up to 1.0 nickel, up to 0.75 iron, up to 1.0 silicon, up to 1.0 manganese, up to 0.25 nitrogen, and cobalt.

In another non-limiting embodiment of the present invention, the implant comprises a cobalt alloy comprising, in percent by weight, up to 0.05 carbon, from 26 to 30 chromium, from 5 to 7 molybdenum, up to 0.75 nickel, up to 0.35 iron, up to 0.50 silicon, up to 0.50 manganese, up to 0.15 nitrogen, and cobalt.

In yet another non-limiting embodiment if the present invention, the implant comprises a cobalt alloy comprising, in percent by weight, from 0.15 to 0.35 carbon, from 26 to 30 chromium, from 5 to 7 molybdenum, up to 1.0 nickel, up to 0.75 iron, up to 1.0 silicon, up to 1.0 manganese, up to 0.25 nitrogen, and cobalt.

In still another non-limiting embodiment of an implant according to the present invention, the implant comprises a cobalt alloy, the cobalt alloy having a percent elongation of at least 10 percent and including a first portion having a KHN of at least 560, and a second portion, adjacent the first portion, the second portion having a KHN that is less than the KHN of the first portion. Further, according to this embodiment, the first portion of the cobalt alloy having a KHN of at least 560 can comprise less than 5 atomic percent nitrogen.

Figure 1:
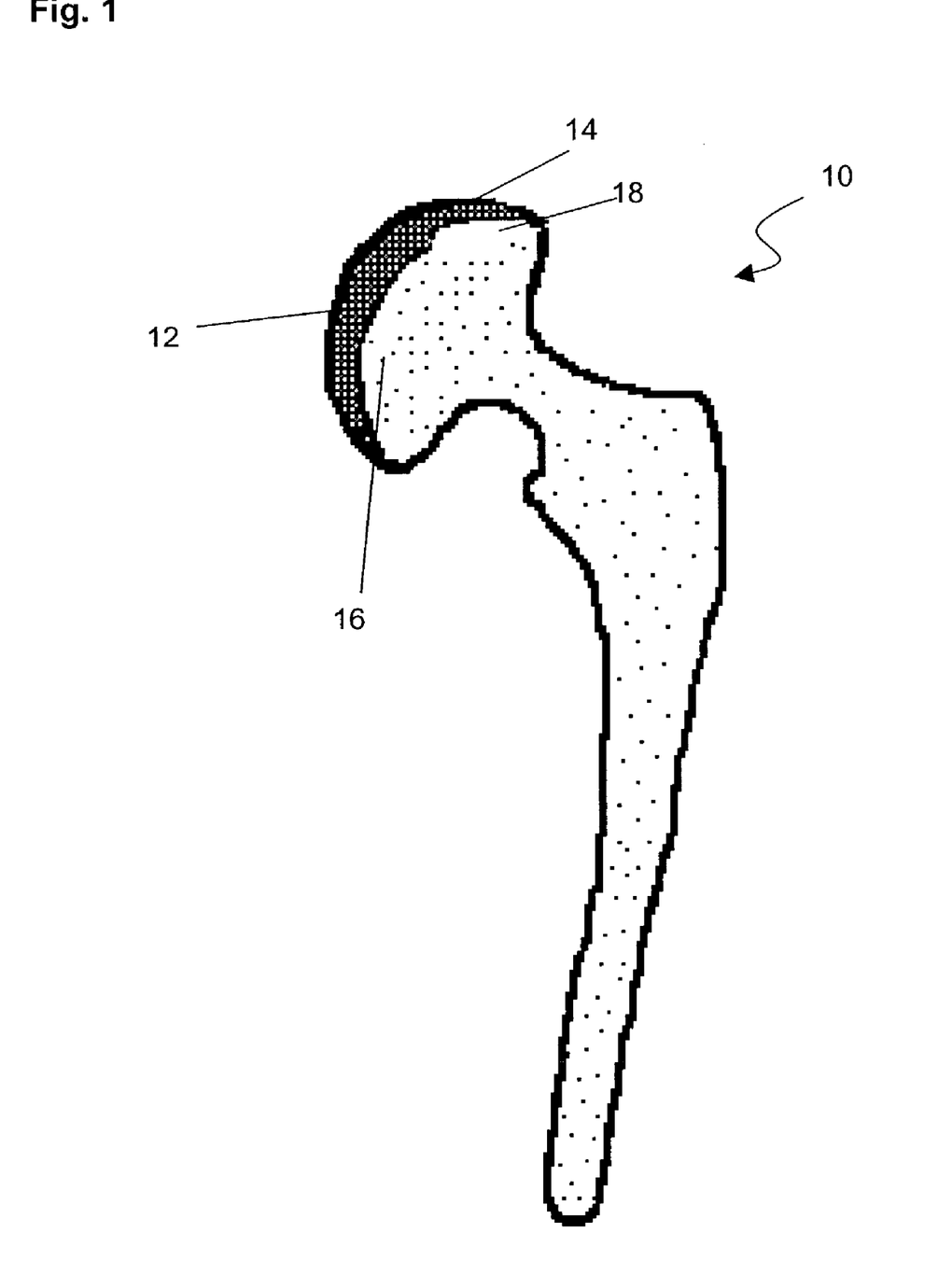
FIG. 1 is a schematic, cross-sectional view of an implant according to certain embodiments of the present invention.

Although not limiting herein, according to the above embodiment, at least a region of a wear surface of the implant can comprise the first portion of the cobalt alloy and a subsurface region of the implant can comprise the second portion of the cobalt alloy. For example, although not limiting herein, as shown in FIG. 1 the implant (which is shown schematically in cross-section), generally designated as 10, can comprise a wear surface 12, and a subsurface region 16. The wear surface 12 of implant 10 can comprise a first portion 14 of cobalt alloy having a KHN of at least 560 and the subsurface region 16, adjacent the wear surface 12, can comprise a second portion 18 of the cobalt alloy having a KHN less than the first portion 14 of the cobalt alloy, as indicated schematically by the shading in FIG. 1.

The non-limiting embodiments of the present invention further include articles of manufacture comprising a cobalt alloy comprising up to 0.35 weight percent carbon, from 26 to 30 weight percent chromium, from 5 to 7 weight percent molybdenum, up to 1.0 weight percent nickel, up to 0.75 weight percent iron, up to 1.0 weight percent silicon, up to 1.0 weight percent manganese, up to 0.25 weight percent nitrogen, and cobalt; the cobalt alloy having a hardness of at least Rockwell C 50 and/or a KHN of at least 560. Non-limiting examples of articles of manufacture according to the present invention include, but are not limited to: orthopedic implants including, but not limited to, hip and knee joints implants; shoulder implants; spinal components and devices including, but not limited to, articulating components; cardiovascular components and devices including, but not limited to, wires, cables, and stents; and fracture fixation devices including, but not limited to plates and screws.

Embodiments of the present invention will now be illustrated by the following specific, non-limiting examples.

EXAMPLES

Example 1

An ingot of a cobalt alloy having the low-carbon, "Alloy 1" composition given in ASTM F1537-00 was prepared as follows. The alloy was vacuum induction melted and subsequently refined in an electroslag reduction process, as well known in the art. The resulting ingot was thermomechanically processed by hot rolling into a bar having a diameter of approximately 0.39 inches. The bar was subsequently cold worked by cold drawing to achieve a 20 percent reduction in area. Thereafter, samples taken from the cold worked bar were subjected to aging treatments as indicated in Table 1 below.

The following properties were measured on both the as-drawn and as-aged bars: ultimate tensile strength ("UTS"), 0.2% off-set yield strength ("0.2% YS"), percent elongation ("Elong %"), percent reduction in area ("RA %"), and Rockwell C hardness ("HRC"). The UTS, 0.2% YS, Elong %, and RA % were determined according to ASTM E8-01. The HRC values were determined according to ASTM E18-02. For comparison, the average value for UTS, 0.2% YS, Elong %, and % RA for 322 conventionally warm worked ("As-Rolled") bars is also included in Table 1.

TABLE 1

| Aging Temperature (° F.) | Aging Time (Hours) | UTS (Ksi) | 0.2% YS (Ksi) | Elong. % | % RA | HRC |
|---|---|---|---|---|---|---|
| As-Rolled | — | 191.1 | 136.2 | 27.1 | 24.8 | 41.0 |
| As-Drawn | — | 256.5 | 208.4 | 10.8 | 19.0 | 48.2 |
| 900 | 1 | 293.6 | 208.9 | 6.4 | 12.5 | — |
| 1000 | 1 | 304.1 | 228.9 | 5.7 | 14.7 | — |
| 1100 | 1 | 295.2 | 231.0 | 5.4 | 13.5 | 55.0 |
|  | 24 | 286.7 | 233.0 | 4.0 | 11.2 | 55.0 |
| 1200 | 1 | 281.8 | 219.0 | 5.5 | 10.0 | 53.5 |
|  | 24 | 265.8 | 240.3 | 3.7 | 4.9 | 53.0 |
| 1300 | 1 | 262.1 | 193.3 | 2.2 | 5.4 | 53.5 |
|  | 24 | 239.2 | 201.9 | 3.4 | 3.7 | 52.3 |
| 1400 | 1 | 226.1 | 165.2 | 3.8 | 7.4 | 52.5 |
|  | 24 | 194.6 | 154.2 | 2.0 | 5.5 | 51.5 |
| 1500 | 1 | 193.6 | 134.4 | 1.5 | 3.2 | 48.5 |
|  | 24 | 215.9 | 143.9 | 7.9 | 9.5 | 48.5 |
| 1600 | 1 | 193.4 | 110.8 | 10.1 | 20.7 | 38.9 |
|  | 24 | 192.9 | 101.3 | 11.6 | 10.7 | 43.6 |
| 1700 | 1 | 197.6 | 149.9 | 14.8 | 18.4 | 41.4 |
|  | 24 | 183.3 | 137.1 | 8.8 | 10.8 | 43.0 |
| 1800 | 1 | 196.8 | 142.4 | 16.0 | 17.3 | 38.0 |
| 1850 | 1 | 172.0 | 119.2 | 19.8 | 30.6 | 36.0 |
| 1900 | 1 | 183.1 | 106.5 | 27.7 | 27.6 | 33.1 |
| 2000 | 1 | 137.1 | 79.3 | 20.0 | 18.2 | 29.0 |

As can be seen from Table 1, both the UTS and 0.2% YS values for the as-drawn (i.e., cold worked, but unaged) sample is higher than the average UTS and 0.2% YS for the as-rolled (i.e., warm worked only) sample. Further, although the Elong. % and % RA for the as-drawn sample is lower than the average values for the as-rolled samples, it is believed that the ductility of the as-drawn material is still acceptable for many applications, including medical implant applications.

The samples that were aged at temperatures up to about 1500° F. from 1 to 24 hours also displayed higher UTS and 0.2% YS values than the average UTS and 0.2% YS values for the as-rolled samples. As compared to the as-drawn sample, the samples that were aged from 1 to 24 hours at a temperature of up to about 1200° F. had higher UTS, 0.2% YS, and HRC values. Further, improved HRC values as compared to the as-drawn sample were also observed after aging from 1 to 24 hours at temperatures up to about 1500° F.

Although not limiting herein, it is believed that for certain medical implant applications where it is desirable have increased UTS, 0.2% YS, and HRC values while maintaining at least a minimum level of ductility in the cobalt alloy, for this particular alloy, aging for 1 to 24 hours at a temperature up to about 1200° F. appears to give suitable properties. Additionally for this particular alloy, although not limiting herein, where higher HRC values are desired, aging for 1 to 24 hours at a temperature of about 1100° F. can provide HRC values greater than 50, and may provide HRC values of at least 53.

Example 2

An additional cobalt alloy bar formed as described above in Example 1 was selectively cold worked as follows. An as-rolled and centerless ground bar was commercially shot peened with a number 550 shot to an intensity of 0.008 to 0.0012 with 400 percent coverage. After shot peening, the bar was heat treated at 1100° F. for 1 hour and air cooled. A cross sectional sample was cut from the aged bar and prepared for microhardness testing. Knoop microhardness readings were taken according to ASTM E384-99, using a 300-gram load. The first Knoop microhardness reading was taken as close as possible to the exterior of the sample, with subsequent readings being in 0.05 mm increments progressing toward the center of the sample, i.e. toward the core of the bar. The results of the Knoop microhardness tests are presented below in Table 2 as a function of distance away from the exterior of the sample.

TABLE 2

| Distance From Exterior of Sample (mm) | Knoop Hardness Number (using 300 g load) |
| --- | --- |
| 0.05 | 624 |
| 0.1 | 571 |
| 0.15 | 547 |
| 0.2 | 560 |
| 0.25 | 554 |
| 0.3 | 539 |
| 0.35 | 554 |
| 0.4 | 556 |
| 0.45 | 550 |

As can be seen from Table 2, portions of the surface of the bar have a higher hardness than the subsurface regions of the bar. The depth of hardening in Example 2 is believed to be consistent with the depth of maximum residual stress observed from shot peening. However, it is believed that deeper hardening results can be expected with other selective cold working processes, such as, but not limited to, the laser peening process, which is believed to be capable of imparting a 4-fold increase in the depth of maximum residual stresses.

Example 3

A cobalt alloy bar was prepared by warm rolling. Samples were taken for tesing in the warm rolled condition ("Comparative Sample") and after aging at 1100° F. for 1 hour and 24 hours ("Sample A"). The remainder of the bar was cold worked by cold rolling to achieve a 20% reduction in area, followed by aging at 1100° F. for 1 hour ("Sample B"). Room temperature tensile and hardness tests were performed on each of the samples. The results of these tests are presented below in Table 3.

TABLE 3

| Sample | Aging Temperature (° F.) | Aging Time (Hours) | UTS (Ksi) | 0.2% YS (Ksi) | Elong % | % RA | HRC |
| --- | --- | --- | --- | --- | --- | --- | --- |
| Comparative Sample | — | — | 201.9 | 129.9 | 27.3 | 23.7 | 41 |
|  | — | — | 208.1 | 130.8 | 26.2 | 22.6 | — |
| A | 1100 | 1 | 209.9 | 135.3 | 30.4 | 28.5 | 43 |
|  | 1100 | 24 | 212.2 | 142.9 | 36.7 | 35.6 | 44 |
| B | 1100 | 1 | 332.0 | 269.0 | 3.0 | 10.1 | 56 |
|  | 1100 | 1 | 330.0 | 272.0 | 3.0 | 10.0 | 56 |

As can be seen from Table 3, Sample B shows a large increase in strength and hardness as compared to both the Comparative Sample and Sample A. Similar increases strength and hardness were not observed for Sample A as compared to the Comparative Sample. In fact, the tensile strength and hardness values observed for Sample A are typical of warm worked material.

Although not limiting herein, it is believed that the properties of the cold worked regions of a cobalt alloy that has been selectively cold worked according to various embodiments of the present invention, will be similar to the properties of Sample B, after the selectively worked cobalt alloy is aged; while the properties of the unselected regions of the selectively cold worked cobalt alloy (i.e., the regions that were not selectively cold worked) will be similar to the properties of Sample A after aging.

Example 4

Fatigue tests were conducted on the Sample B material (described above in Example 3) after aging the material at 1100° F. for 1 hour. The runout stress after $10^7$ cycles in fully reversed bending (R=−1) for the Sample B material was determined at room temperature using a smooth rotating beam fatigue test. The results of the fatigue test are presented in Table 4 below, along with the results for a similar test conducted on the material of the Comparative Sample of Example 2.

TABLE 4

| Sample | Runout Stress for $10^7$ Cycles |
| --- | --- |
| Comparative Sample | 110-115 ksi |
| Sample B | 160-164 ksi |

As can be seen from the results presented in Table 4, Sample B, which was processed according to one embodiment of the present invention, has a higher runout stress than the Comparative Sample.

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, those of ordinary skill in the art will, upon considering the foregoing description, recognize that many modifications and variations of the invention may be employed. All such variations and modifications of the invention are intended to be covered by the foregoing description and the following claims.

We claim:

1. A method of processing a cobalt alloy comprising from 26 to 30 weight percent chromium, from 5 to 7 weight percent molybdenum, up to 1.0 nickel, up to 0.75 iron, up to 1.0 manganese, and greater than 50 weight percent cobalt, the method comprising:
   cold working the cobalt alloy to achieve a total reduction of 5 to 25 percent; and
   aging the cold worked cobalt alloy at a temperature ranging from 900° F. to 1300° F. for a time period ranging from 1 hour to 24 hours;
   wherein after aging the cold worked cobalt alloy, the cobalt alloy has a hardness of at least Rockwell C 50, an elongation of at least 2.2 percent, and an ultimate tensile strength of at least 260 kilopounds per square inch.

2. The method of claim 1 wherein after cold working the cobalt alloy, at least a portion of the cobalt alloy comprises an fcc phase matrix with one or more regions of an hcp phase distributed in the fcc phase matrix.

3. The method of claim 1 wherein the cold working comprises at least one of rolling, drawing, swaging, shot peening, and laser peening.

4. The method of claim 1 wherein the cold worked cobalt alloy is aged at a temperature ranging from 1000° F. to 1200° F.

5. The method of claim 4 wherein after aging the cold worked cobalt alloy, the cobalt alloy has a hardness of at least Rockwell C 53.

6. The method of claim 4 wherein after aging the cold worked cobalt alloy, the cobalt alloy has a 0.2%-offset yield strength of at least 210 kilopounds per square inch.

7. The method of claim 1 wherein the cobalt alloy has a runout stress for 107 cycles in fully reversed bending of at least 130 kilopounds per square inch.

8. The method of claim 1 wherein the cold working comprises drawing.

9. The method of claim 8 wherein the drawing is conducted such that the cobalt alloy has a total reduction in area ranging from 10 percent to 25 percent.

10. The method of claim 1 wherein the cold working comprises rolling.

11. The method of claim 10 wherein the rolling is conducted such that the cobalt alloy has a total reduction in thickness ranging from 10 percent to 25 percent.

12. The method of claim 1 wherein the cobalt alloy further comprises, in percent by weight, up to 0.14 carbon, up to 1.0 silicon, and up to 0.25 nitrogen.

13. The method of claim 1 wherein the cobalt alloy further comprises, in percent by weight, up to 0.05 carbon, up to 0.35 iron, up to 0.50 silicon, up to 0.50 manganese, and up to 0.15 nitrogen.

14. The method of claim 1 wherein the cobalt alloy further comprises, in percent by weight, from 0.15 to 0.35 carbon, up to 1.0 silicon, and up to 0.25 nitrogen.

15. The method of claim 1 wherein the cobalt alloy further comprises, in percent by weight, up to 0.35 carbon, up to 1.0 silicon, and up to 0.25 nitrogen.

16. The method of claim 15, wherein the cobalt alloy is at least a portion of an implant.

17. The method of claim 15, wherein the cobalt alloy is at least a portion of an article of manufacture selected from the group consisting of: an orthopedic implant; a hip joint implant; a knee joint implant; a shoulder implant; a spinal component; a spinal device; a spinal articulating component; a cardiovascular component; a cardiovascular device; a cardiovascular wire; a cardiovascular cable; a cardiovascular stent; a fracture fixation device; a fracture fixation plate; and a fracture fixation screw.

18. The method of claim 1, wherein the cobalt alloy is at least a portion of an implant.

19. The method of claim 1, wherein the cobalt alloy is at least a portion of an article of manufacture selected from the group consisting of: an orthopedic implant; a hip joint implant; a knee joint implant; a shoulder implant; a spinal component; a spinal device; a spinal articulating component; a cardiovascular component; a cardiovascular device; a cardiovascular wire; a cardiovascular cable; a cardiovascular stent; a fracture fixation device; a fracture fixation plate; and a fracture fixation screw.

20. A method of processing a cobalt alloy, the method comprising cold working a cobalt alloy including, in percent by weight, from 26 to 30 chromium, from 5 to 7 molybdenum, from 0.15 to 0.35 carbon, up to 0.75 nickel, up to 0.35 iron, up to 0.50 silicon, up to 0.50 manganese, up to 0.15 nitrogen, and cobalt to achieve a total reduction of 5 to 25 percent, wherein after cold working, the cobalt alloy has a hardness of at least Rockwell C 45.

21. A method of processing a cobalt alloy, the method comprising cold working a cobalt alloy including, in percent by weight, from 26 to 30 chromium, from 5 to 7 molybdenum, up to 0.05 carbon, up to 0.75 nickel, up to 0.35 iron, up to 0.50 silicon, up to 0.50 manganese, up to 0.15 nitrogen, and cobalt to achieve a total reduction of 5 to 25 percent, wherein after cold working, the cobalt alloy has a hardness of at least Rockwell C 45, and further wherein after aging the cobalt alloy, the cobalt alloy has an ultimate tensile strength of at least 260 kilopounds per square inch.

22. The method of claim 21, wherein the cobalt alloy is at least a portion of an implant.

23. The method of claim 21, wherein the cobalt alloy is at least a portion of an article of manufacture selected from the group consisting of: an orthopedic implant; a hip joint implant; a knee joint implant; a shoulder implant; a spinal component; a spinal device; a spinal articulating component; a cardiovascular component; a cardiovascular device; a cardiovascular wire; a cardiovascular cable; a cardiovascular stent; a fracture fixation device; a fracture fixation plate; and a fracture fixation screw.

* * * * *